US011413154B2

(12) United States Patent
Wagner et al.

(10) Patent No.: US 11,413,154 B2
(45) Date of Patent: Aug. 16, 2022

(54) STEMLESS SHOULDER IMPLANT WITH BUTTON LOCK

(71) Applicant: Howmedica Osteonics Corp., Mahwah, NJ (US)

(72) Inventors: Thomas Chad Wagner, Huntersville, NC (US); Rajan Yadav, New Delhi (IN); Sunny Shorabh, Ghaziabad (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/993,673

(22) Filed: Aug. 14, 2020

(65) Prior Publication Data

US 2021/0045887 A1    Feb. 18, 2021

Related U.S. Application Data

(60) Provisional application No. 62/886,439, filed on Aug. 14, 2019.

(51) Int. Cl.
*A61F 2/40* (2006.01)
*A61B 34/10* (2016.01)
*A61F 2/30* (2006.01)

(52) U.S. Cl.
CPC .. *A61F 2/4081* (2013.01); *A61F 2002/30461* (2013.01); *A61F 2002/4085* (2013.01)

(58) Field of Classification Search
CPC ............ A61F 2002/30011; A61F 2002/30604; A61F 2/40; A61F 2/4612; A61F 2/4081; A61F 2002/30461; A61F 2002/4085; A61F 2002/4018; A61F 2002/30784; A61F 2002/30878; A61F 2002/30892; A61F 2002/30884; A61F 2002/30578;
(Continued)

(56) References Cited

U.S. PATENT DOCUMENTS 6,770,100 B2 * 8/2004 Draenert .................. A61F 2/36
                                                    623/23.26
8,734,491 B2   5/2014 Seavey
(Continued)

OTHER PUBLICATIONS

FibuLock Nail, Ankle Fracture System, Surgical Technique, Sonoma Orthopedic Products, Inc, 2015, pp. 1-28.
(Continued)

*Primary Examiner* — Ann Schillinger
(74) *Attorney, Agent, or Firm* — Lerner, David, Littenberg, Krumholz & Mentlik, LLP

(57) ABSTRACT

A system for shoulder repair includes a prosthetic stemless shoulder implant including a base member extending along a longitudinal axis from a first side to a second side. The second side adapted to engage bone of a patient. The base member defines a hole that extends along the longitudinal axis and through the second side of the base member for receiving a flexible member therethrough. The system includes a fixation construct including a first fixation device and a second fixation device, the first and second fixation devices connected by the flexible member. While the first fixation device is positioned outside of the second side of the base member and the second fixation device is positioned within the base member, the flexible member is adapted to tension the first fixation device with respect to the second fixation device.

18 Claims, 10 Drawing Sheets

(58) Field of Classification Search
CPC ........ A61F 2002/30332; A61F 2/30749; A61F 2/30771; A61F 2/4003
See application file for complete search history.

(56) References Cited

U.S. PATENT DOCUMENTS

| | | | | |
|---|---|---|---|---|
| 8,876,900 | B2 * | 11/2014 | Guederian | A61B 17/0401 |
| | | | | 623/13.17 |
| 9,289,304 | B1 * | 3/2016 | Kaufmann | A61F 2/30 |
| 10,076,377 | B2 * | 9/2018 | Bonutti | A61B 17/12131 |
| 2008/0183297 | A1 * | 7/2008 | Boileau | A61B 17/1635 |
| | | | | 623/16.11 |
| 2009/0287309 | A1 * | 11/2009 | Walch | A61L 27/16 |
| | | | | 623/18.11 |
| 2009/0292364 | A1 * | 11/2009 | Linares | A61B 17/686 |
| | | | | 623/19.13 |
| 2012/0191202 | A1 * | 7/2012 | Borowsky | A61F 2/4684 |
| | | | | 623/19.11 |
| 2015/0190237 | A1 * | 7/2015 | Bonin, Jr. | A61F 2/40 |
| | | | | 623/19.14 |
| 2016/0206436 | A1 * | 7/2016 | Chavarria | A61F 2/4059 |
| 2017/0209196 | A1 * | 7/2017 | Zajac | A61B 17/842 |

OTHER PUBLICATIONS

Sapio et al., U.S. Appl. No. 60/021,377, filed May 7, 2020, titled "Stemless Metaphyseal Humeral Implant".

* cited by examiner

STEMLESS SHOULDER IMPLANT WITH BUTTON LOCK

CROSS-REFERENCE TO RELATED APPLICATIONS

This application claims the benefit of the filing date of U.S. Provisional Patent Application No. 62/886,439, filed Aug. 14, 2019, the disclosure of which is hereby incorporated herein by reference as if fully set forth herein.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

It is often preferable to maintain as much of a patient's natural bone stock as possible during such a procedure. Prostheses generally have a certain life expectancy and in certain cases need to be replaced at some point. If one or more prostheses need to be removed and/or replaced in a revision procedure, a large bone void could be left after their removal. In certain cases, this bone void is not ideal for receipt of revision components. Preserving natural bone stock may be desirable for the ability to even perform a revision procedure.

In total or partial arthroplasty surgery, stemmed prostheses are often used which generally include a long stem that passes through a center of a long bone, the stem helping to anchor the remaining components of the prosthesis. However, stemmed prostheses may result in a large amount of healthy bone being removed in order to accommodate the stem. In some cases, stemless prostheses may be used, which may result in less healthy bone stock being removed. However, in some cases stemless prostheses may not anchor the particular prosthesis as well as a stemmed prosthesis would.

Thus, there is a need to enhance the fixation of the immediate and the long term fixation of prostheses, including stemless and stemmed prostheses.

BRIEF SUMMARY

According to a first embodiment of the present disclosure, a system for shoulder repair includes a prosthetic stemless shoulder implant including a base member extending along a longitudinal axis from a first side to a second side. The second side adapted to engage bone of a patient. The base member defines a hole that extends along the longitudinal axis and through the second side of the base member for receiving a flexible member therethrough. The system includes a fixation construct including a first fixation device and a second fixation device, the first and second fixation devices connected by the flexible member. While the first fixation device is positioned outside of the second side of the base member and the second fixation device is positioned within the base member, the flexible member is adapted to tension the first fixation device with respect to the second fixation device.

In other embodiments, the first fixation device may be an oblong button having a plurality of apertures for receiving the flexible member. The second fixation device may have a round button having a plurality of apertures for receiving the flexible member. The hole may have a first diameter and the second fixation device may have a second diameter, the second diameter being larger than the first diameter such that the second fixation device is prevented from passing through the hole. The first fixation device may have a first dimension that is less than the first diameter such that the first fixation device is sized to pass through the hole of the base member when in a first position, and the first fixation device may have a second dimension that is greater than the first diameter such that the first fixation device is prevented from passing through the hole of the base member when in a second position. The base member may include a tapered opening for receiving a prosthetic humeral head component of the prosthetic stemless shoulder implant. The hole and the opening may be coaxial and the hole may have a diameter smaller than a smallest diameter of the opening. The second fixation device may be sized to be positionable within the tapered opening of the base member. The flexible member may be a suture.

According to another embodiment of the present disclosure, a method for shoulder surgery includes the steps of implanting a base member of a prosthetic stemless shoulder implant into a proximal humerus of a patient; drilling through a surface of the base member and through the humerus to form a passageway from the proximal humerus through a cortical shell of the humerus; passing a first fixation device of a fixation construct through the passageway so that the cortical shell is positioned between the base member and the first fixation device; placing a second fixation device of the fixation construct in the base member, the first fixation device being coupled to the second fixation device via a flexible member; and tensioning the flexible member to secure the base member to the proximal humerus via the fixation construct. In other embodiments, the method may include the step of flipping the first fixation device so that a surface lies flush against the cortical shell of the humerus. The method may include the step of tying at least one locking knot with the flexible member extending proximally to the second fixation device. The tying step may include tying three locking knots. The method may include the step of attaching a humeral head member to the base member.

According to another embodiment of the present disclosure, a system for shoulder repair includes a base component having a proximal collar having a proximal surface and a bone-engaging surface opposite the proximal surface, a central anchor extending distally from the bone-engaging surface, and a connection member having threads; and a lateral component having a head and a shaft extending from the head, at least a portion of the shaft having threads for engagement with the threads of the connection member.

In other embodiments, the threads of the connection member may be external threads. The threads of the shaft may be internal threads on the shaft. The threads of the connection member may be internal threads. The threads of the shaft may be external threads.

DETAILED DESCRIPTION

Figure 1:
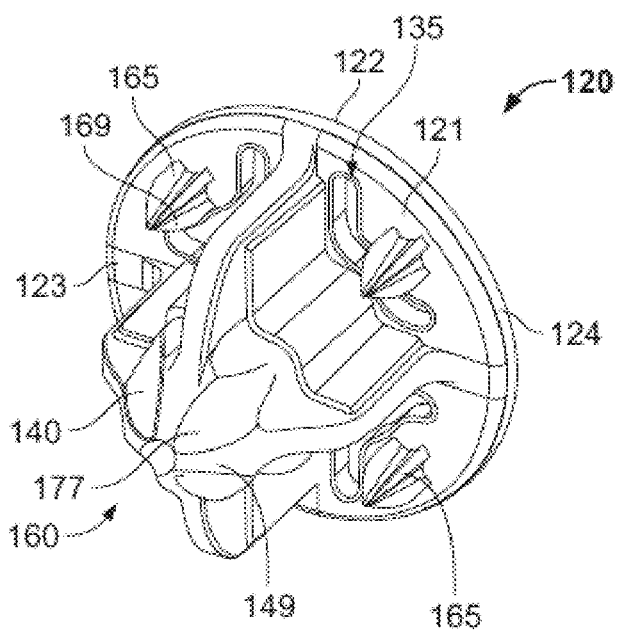
FIG. 1 is a perspective side view of a base component of a shoulder repair system according to an embodiment of the present disclosure.
Figure 2:
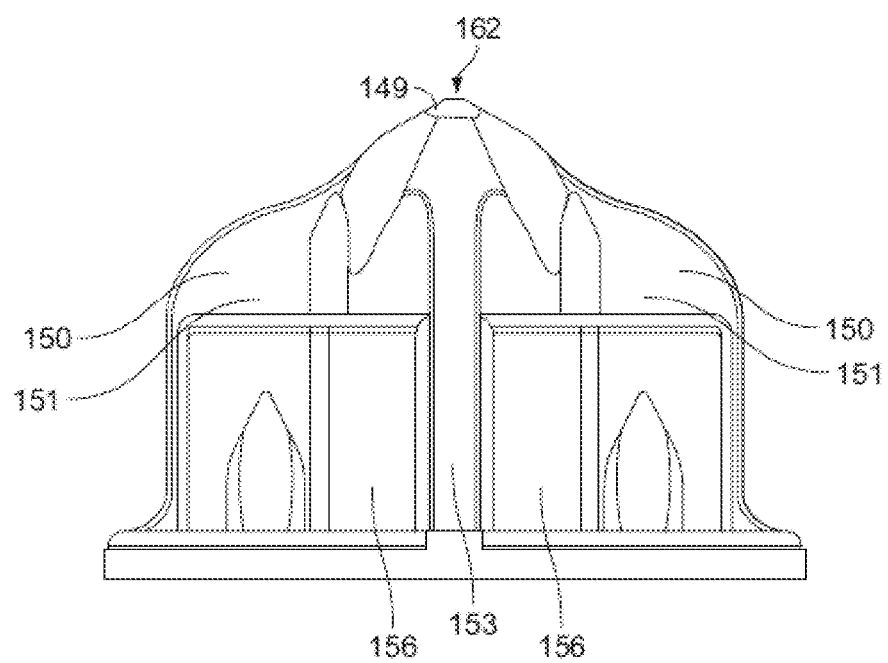
FIG. 2 is a side view of the base component of FIG. 1.

It should be understood that although the term "stemless implant" is used herein, the term does not indicate that a stemless implant fully lacks any anchor, but rather a stemless implant may include an anchor that is significantly smaller and/or shorter than stems of typical known stemmed implants. Further, the stemless implants of the present disclosure generally include a base member intended for coupling to an end of a first bone of a joint, such as a humerus or femur, and an articulating member intended to attach to the base member and to provide articulation with the second bone of the joint (or a corresponding prosthesis attached to the second bone). Further, as used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner Although certain orientations are described herein with reference to proximal/distal directionality, this description is intended to set forth an example and not intended limit the scope of the orientation of such arrangements. For example, the orientation of the system may be such that the system extends in a direction that is generally in the anterior/posterior direction or medial/lateral direction. As a result, the terms are intended to refer to opposing sides of the implant, regardless of its orientation within the body.

A first embodiment of the present disclosure includes shoulder repair system 100 which includes prosthetic shoulder base component 120 and fixation construct 180. Prosthetic shoulder component 120 is a base component of a stemless implant which may be used in conjunction with a humeral head component for a shoulder repair surgery. Although shown as a stemless implant, the base component may instead be a stemmed implant having similar features to those described below. Base component 120 includes collar 121 and central anchor 140 extending distally from the collar along a longitudinal axis to distal end 149. Collar 121 is generally annular and includes first or proximal end surface 122, second or distal bone-engaging surface 123 and side surface 124 connecting the proximal end surface 122 and the distal bone-engaging surface 123. Although shown as having a generally annular shape, collar 121 may be have other shapes, for example the collar may be generally rectangular, trapezoidal, triangular, etc.

Anchor 140 includes a plurality of ribs 150, each rib projecting radially outward of distal end 149 and extending to the bone-engaging surface 123. Each rib 150 includes two lateral side walls 151 and curved outer surface 153 between the two lateral side walls 151. Lateral side walls 151 may be flat, concave, and/or convex. The outer surface 153 is rounded which may provide more surface to create bone in-growth after implantation of the base component 120. Anchor 140 includes connecting surfaces 156 extending from distal end 149 to bone-engaging surface 123 and positioned between and connecting two adjacent ribs 150. Near distal end 149, connecting surface 156 include tapered grooves 177 which form a slot to receive bone-ingrowth after implantation.

Base component 120 includes four ribs 150 that form a general "x" or "cross" shape with each rib being spaced equally apart from each adjacent rib by 90 degrees. However, it should be understood that other angles between the pairs of adjacent ribs may be suitable. Alternatively, there may be more or less ribs 150 in various arrangements on distal end 149.

Figure 5:
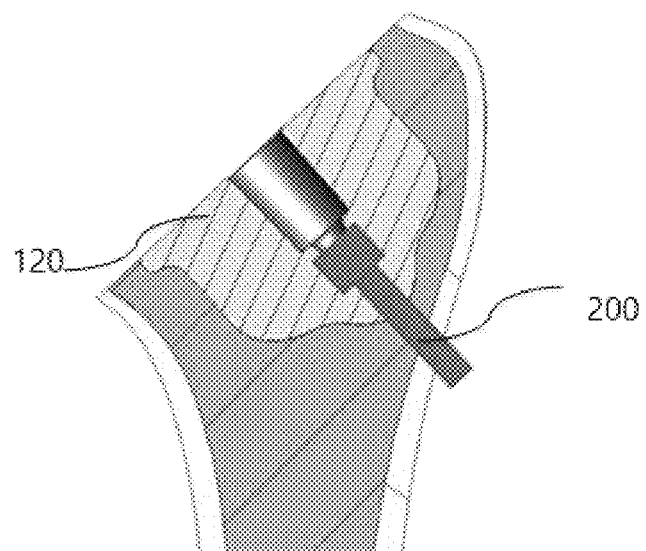
FIG. 5 is a schematic cross-section of the base component of FIG. 1 implanted within the humerus in conjunction with a drilling tool according to a method of use of an embodiment of the present disclosure.

Base component 120 is cannulated and includes an opening with a connection portion, such as a thread or taper, e.g. Morse taper, for connection to an articulating prosthetic component, such as a prosthetic humeral head, and preferably also with an instrument to facilitate the removal of the base during a revision surgery, such as by pulling out the implant or using a slap hammer Opening 160, shown in FIG. 5, extends entirely through the base component along its longitudinal axis such that opening 160 extends through proximal surface 122 and through distal end 149 of anchor 140 to define a bore through the base component. Bore or opening 160 has a first portion 160a adjacent the proximal surface 122 of the base component and a second portion 160b which terminates at a hole 162 at the distal end of the second portion 160b which has a second diameter that is less than a first diameter of the first portion 160a. Hole 162 is coaxial with first portion 160a. At the transition from first portion 160a to second portion 160b, opening 160 includes shoulder 163, shown in FIG. 5.

Collar 121 includes a plurality of peripheral anchors or pegs 165 extending distally from bone-engaging surface 103 to distal tips 169. Pegs 165 are positioned radially outwardly of connecting surfaces 156. Pegs 165 are relatively shorter than central anchor 140 such that anchor 140 extends a first distance from bone-engaging surface 103 to distal end 149 and pegs extend a second distance from bone-engaging surface 103 to distal tips 169 that is less than the first distance. The use of at least four pegs 165, as shown, may provide for enhanced feedback, especially compared to the use of three or fewer pegs, while seating base component 120 into the prepared bone during insertion. For example, upon initial contact of pegs 165 with a prepared flat bone surface, the surgeon may be able to easily determine if each of the pegs is simultaneously in contact with the bone. In particular, if all four pegs 165 are in contact with the proximal surface of the bone, the base component 120 should not experience any significant amount of rocking or tilting.

Base component 120 includes one or more enhanced fixation surfaces on portions of anchor 140 and bone engaging surface 103. The enhanced fixation surface may also be positioned on portions of pegs 165. Generally, the enhanced fixation surface is positioned on proximal portions of the anchor 140 and bone engaging surface 103. The enhanced fixation surface may take the form of a porous metal surface, such as a porous titanium alloy, including Tritanium® by Howmedica Osteonics Corporation. The porous portion of the base component 120 helps facilitate bone ingrowth into the anchor to increase long term fixation and stability of the component in the bone.

Collar 121 includes a plurality of chisel slots 135 extending through bone-engaging surface 123 to proximal surface 122 to aid in a revision procedure after the base component 120 has been implanted within a patient. In the illustrated embodiment, there are four chisel slots 135 with each chisel slot positioned radially between a connecting surface 156 and a peg 165. Each chisel slot 135 is also positioned between two adjacent ribs 150. With this positioning of chisel slots 135, a surgeon may insert a tool into each chisel slot 135 in order to chisel, ream, or otherwise cut away at bone that is adjacent to pegs 165, surfaces 156, and ribs 150. This positioning of the chisel slots 135 allows for loosening of the bone ingrowth on enhanced fixation surfaces, which provides for easier removal of the base component 120 so that a new device may be implanted in its place, as discussed in greater detail below.

While certain features of the base component may help to facilitate bone ingrowth in the anchor for fixation of the component in bone, the base component may lack the desired level of securement during the period after the component is implanted in a patient but before bone ingrowth has occurred. Typically, the bone ingrowth process can take up to 10 weeks to securely fix a component in bone, and during this interim time period, e.g. within the first ten weeks after implantation, the component may experience micro-motions or slight movements which may ultimately reduce or even prevent proper bone ingrowth and biologic healing.

System 100 provides for immediate mechanical fixation and further includes fixation construct 180 which includes first fixation device or first button 184 and second fixation device or second button 188 connected by flexible member or suture 190 which is configured to tension the first button with respect to the second button or vice versa.

Figure 3:
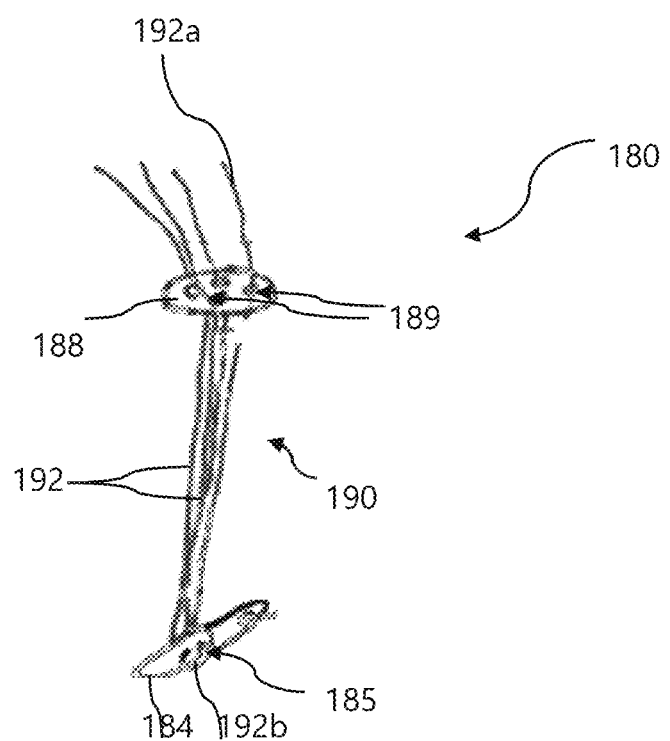
FIG. 3 is a side view of a fixation construct for use in conjunction with the base component of FIG. 1 in the shoulder repair system.
Figure 4:
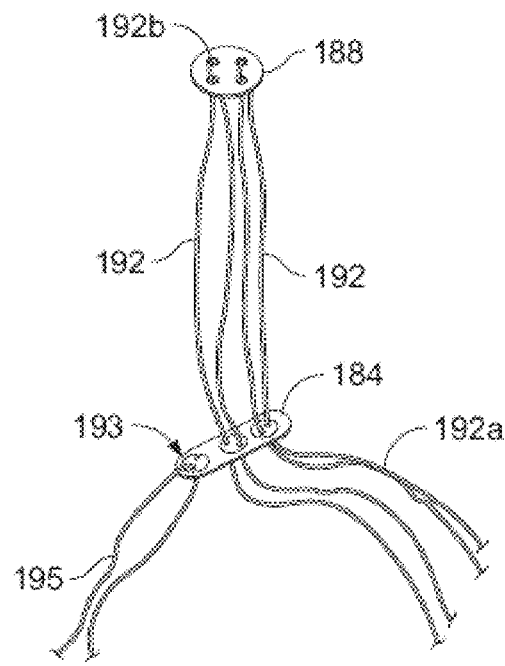
FIG. 4 is a side view of the fixation construct of FIG. 3 in an alternative arrangement.

FIGS. 3 and 4 show flexible member 190 in the form of suture having a plurality of strands 192 shown in conjunction with first and second buttons 184, 188. First and second buttons 184, 188 each has a plurality of apertures 185, 189, respectively for receiving the strands 192 of suture 190 through the aperture to loop the suture back around to connect the first and second buttons to each other. Each button 184, 188 has opposing flat surfaces which form the "button" shape and which allow the button to rest flush against a flat in its intended implanted position. In an initial condition, i.e. prior to finalized implantation, the suture can tension the buttons with respect to each other to adjust the distance between the buttons. Tensioning and releasing the suture allows the user to control of the distance that the buttons are spaced apart from each other as well as the tension forces on the buttons in a final, implanted condition. FIG. 3 shows a first arrangement of the fixation construct with suture strands 190 positioned through the apertures of first button 184 and second button 188 such that the suture strands form loops 192b at first button 184 and the free ends 192a extend out of second button 188. FIG. 4 shows an alternative embodiment in which the suture strands 192 form loops 192b at second button 188 and the free ends 192a extend out of first button 184. Additionally, first button 184 may include aperture 193 for receiving lead suture 195 to facilitate the first button 184 to be pulled through the cannulated bone using a leading needle. Other arrangements of fixation constructs, including a first and a second button with a tether therebetween, and methods for tensioning, are disclosed in U.S. Pat. No. 8,734,491 to Seavey, filed on Aug. 24, 2011, the disclosure of which is incorporated herein by reference in its entirety.

First button 184 has a minimum dimension that is less than the second diameter of second portion 160b of the opening 160 of the base component 120. In this way, the first button 184 can pass through hole 162 of second portion 160b of the opening 160 when the first button is in a first orientation. After passing through hole 162, first button 184 is positioned distally outward to a location outside of and spaced away from distal end 149 of anchor 140. Second button 188 has a minimum dimension that is larger than second portion 160b and hole 162 and remains within the anchor and proximal to the distal-most end of the base component.

In the illustrated embodiment, first button 184 has an oblong shape to prevent any snagging or irritation of the bone while allowing the first button to pass through the base component as well as pass through the bone such that in the final configuration, the first button rests against the cortical bone. Second button 188 is round in shape to prevent any snagging or irritation of bone while also preventing the second button from passing through base component. Although, the term button is used, the term is used for convenience only and does not indicate a particular shape. In that regard, any fixation means configured to receive suture strands may be utilized.

In use, base component 120 is implanted within a prepared surface of the bone. As shown in FIG. 4, tool 200 is used to drill through opening 160 of base component 120 and through the cortical shell 400 of the humerus to form a passage for receiving a portion of fixation construct 180. The drilled hole may be about a 1.5 to 3.0 millimeter hole, and preferably the cannulated drill bit is 2.7 mm, although the drill bit and resulting hole may be larger or smaller as desired, including depending on the particular anatomy being treated with the implant. The drilled hole may have a diameter equal to the diameter of second portion 160b, such that it forms one continuous passageway through bone for suture 190 to extend through. The assembled fixation construct 180, e.g. first and second buttons 184, 188 connected by suture 190 is inserted into the drilled hole via a leading needle by passing first through opening 160 and out of the distal end 149 of the anchor. The needle may be about 1.5 mm in diameter, but the needle may be larger or smaller as desired, and preferably has a dimension slightly smaller than the diameter of the drilled hole. First button 184 passes through opening 160 along with the needle such that the maximum dimension is oriented in the direction of the longitudinal axis, e.g. as in this example is in the proximal to distal direction, of base component 120 so that the minimum dimension of first button 184 passes through the hole 162 of anchor 140 and passes out of the base component and through the cortical shell 400 so that the cortical shell 400 of the humerus is positioned between the base component 120 and the first button 184. As button 184 is passed through anchor 140 and into bone, suture 190 follows and passes through hole 162 of anchor 140.

With the arrangement shown in FIG. 3, after first button 184 is passed through hole 162 and out of base component 120 and into bone, a first portion of strands 192 extend distal to hole 162 of anchor 140 and a second portion of strands 192 extend proximal to hole 162 of anchor 140 and can be pulled by the user, e.g. free ends 192a. In this arrangement, suture strands 192 are passed through the apertures 185 of first button 184 and apertures of 189 of second button 188 such that free ends 192a extend from second button 188 and the suture strands form loops 192b at second button 188. First button 184 travels through the drill hole and through the cortical shell, the strands 192 extending proximal to hole 162 of anchor 140 are tensioned to flip first button 184 to fix this leading button at a flush position seated against the cortical shell 400

Alternatively, with the arrangement shown in FIG. 4, after first button 184 is passed through hole 162 or anchor 140, free ends 192a extend distally from first button 184 and loops 192b are positioned proximally of second button 188. Suture strands are tensioned by pulling on the strands to flip first button 184 and cause compression of the first button 184 against the cortex.

In this second, flipped orientation, the maximum dimension of first button 184 extends in a non-parallel (i.e., perpendicular or oblique) to the drill hole and is sized larger than the drill hole to prevent the first button 184 from being pulled back into the drilled hole but rather maintains its position seated against the outer surface of the bone. Suture strands 192 are jockeyed back and forth to move the second button 188 further distally while the first button 184 remains in contact with the cortical shell 400. Suture strands 192 are continued to be jockeyed, e g manipulated with tension by alternately pulling each strand in small increments until the desired tension on the cortex is achieved, to decrease the distance between first and second buttons 184, 188 to draw and compress the second button 188 toward the first button 184. Alternating pulling of different strands of the suture continues to draw the second button 188 toward the first button 184 until second button 188 rests flush inside of the anchor, e.g. flush against shoulder 163. When the second button 188 is flush within the anchor 140, the flexible member 190 can be pulled to apply the desired amount of tension to the fixation construct 180.

Figure 6:
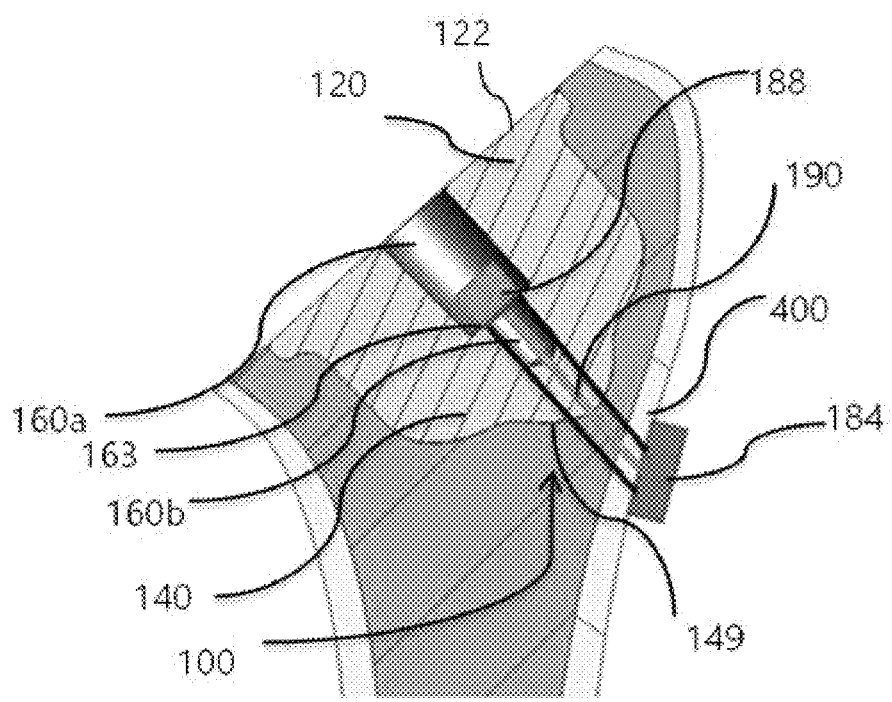
FIG. 6 is a schematic cross-section of the base component of FIG. 1 in conjunction with the fixation construct of FIG. 3 implanted within the humerus.
Figure 7:
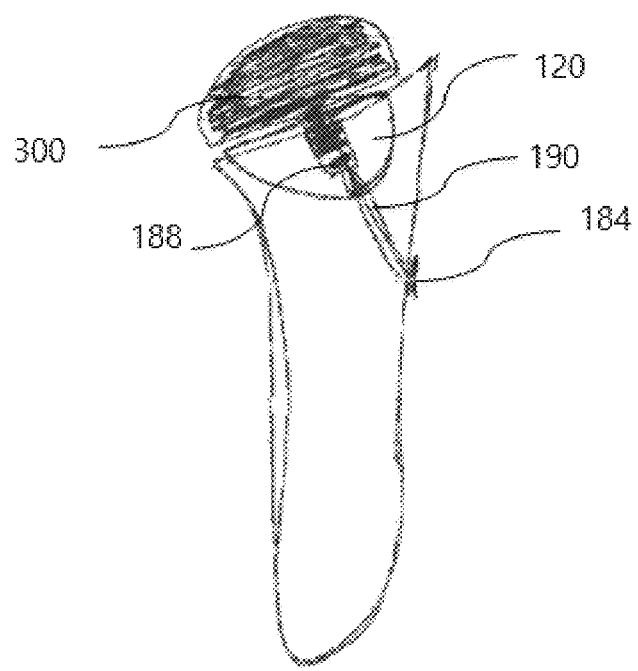
FIG. 7 is a schematic view of the base component of FIG. 1 in conjunction with the fixation construct of FIG. 3 in conjunction within a humeral head component implanted within the humerus.

After tensioning, the fixation construct 180 can be locked by tying one or more locking knots proximally of the second button 188. Two or three knots may be tied for additional securement. Other locking techniques may be employed rather than tying knots to lock the fixation construct in its final position within the base component and the bone. A knot cutter may be used to trim the excess suture. A humeral head component 300 is then implanted by inserting it into the first portion 160a of opening 160, as is shown in FIG. 6. This further locks the fixation construct, namely, the second button 188 in place. In the preferred embodiment, shown in FIG. 4, free ends 192a extend from first button 184 and are cut at the cortex. This is advantageous as it reduces the amount of suture sitting within the anchor. This may enable the humeral head to have a more secure fit within the anchor. Additionally, free ends 192a extending from the cortex allows easier access to cut and tie the strands.

With this configuration, system 100 provides immediate and flexible fixation which increases the likelihood of long-term fixation of the base component. The flexible fixation construct provides immediate stability to the base component to minimize any micro-motion of the component, e.g. a stemless implant or stemmed implant. Reducing the micro-motions allows for proper biological healing and bone ingrowth to provide long-term stability.

Figure 8A:
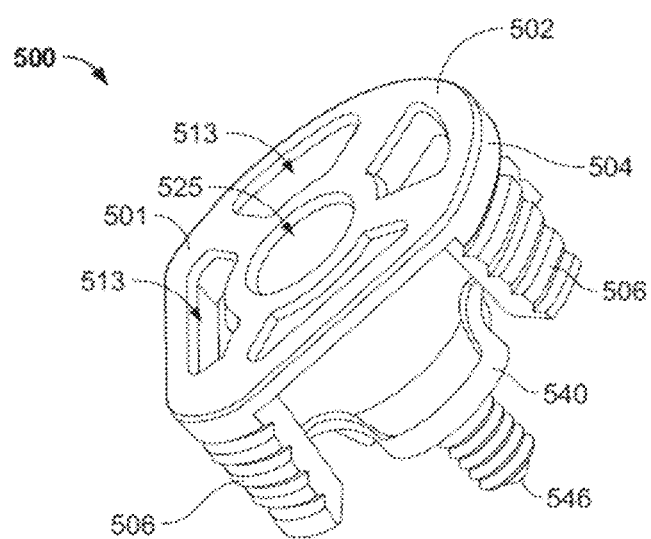
FIGS. 8A and 8B are a perspective side view and a cross-sectional view of a base component in accordance with another embodiment of the present disclosure.
Figure 8B:
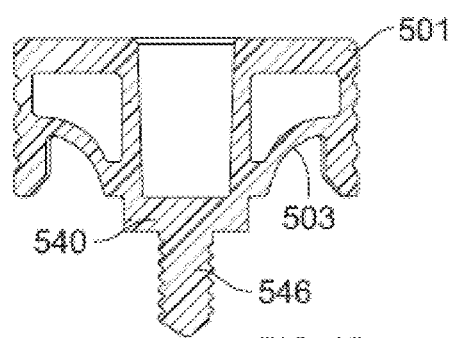
Figure 9:
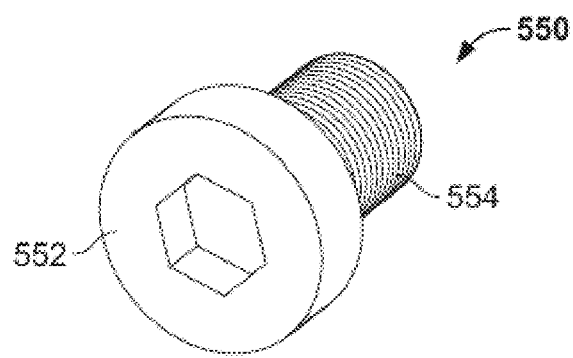
FIG. 9 is a perspective side view of a lateral component for use in conjunction with the base component of FIGS. 8A and 8B.

In another embodiment, shown in FIGS. 8A-B and 9, the system is a two-piece system including a base component 500 that is a proximal humeral component and a second, lateral humeral component 550. Generally, base component 500 is fixed on the resected plane of the cavity prepared within the proximal humerus, and lateral component 550 is inserted from the lateral side of the humerus to lock the base component in position to provide additional stability to the base component. The locking is accomplished via corresponding threads on each of the two components, for example, in this embodiment, base component 500 has male threads extending distally of the anchor, the threads lock with female threads of the lateral component, as described in further detail below.

FIGS. 8A-8B show base component 500 which generally includes collar 501 and central anchor 540 coupled thereto (or integrally formed therewith). Collar 501 includes a proximal end surface 502, a distal bone-engaging surface 503, and side wall 504 extending along the circumference of the collar and extending distal to bone-engaging surface 503. Side wall 504 includes supports 506 extending distally from side wall 504 and from bone-engaging surface 503. Supports 506 are spaced apart from one another around the circumference of the collar 501. Supports 506 may each have a concave inner surface which increases surface area which provides for greater fixation. Further, such concavity increases compression to help achieve a press fit between the base component and the bone which also facilitates greater fixation. Supports 506 may assist in initial fixation of base 500 within the patient. As shown, the outer surfaces of side wall 504 and supports 506 may include ridges to facilitate bone ingrowth of the implanted base 500.

Anchor 540 is positioned generally centrally on collar 501 and extends distally therefrom. As best shown in FIG. 8B, base 500 includes threaded connection member 546 extending distally from anchor 540 for coupling to internally threaded lateral component 550. Connection member 546 includes male threads along an outer surface of the connection member. The threads extend along a substantial portion of the length of the connection member 546.

Base 500 may include one or more enhanced fixation surfaces to allow for greater bone ingrowth into the base 500. The enhanced fixation surfaces may take the form of a porous metal surface, such as porous titanium alloy, including Tritanium® by Howmedica Osteonics Corporation. The enhanced fixation surfaces may be positioned on bone-engaging surface 503 and/or a portion of anchor 540. The enhanced fixation surfaces may be rougher than the adjacent surfaces of bone-engaging surface 503 and anchor 540, resulting in greater friction between the enhanced fixation surface and the bone. This increased friction may help provide additional fixation by providing additional resistance against pull-out forces. When implanted, much of the fixation between the bone and the base 500 may initially result from the interaction between the bone and one or more of the anchor 540 and the supports 506. However, after bone grows into the base 500, including into the enhanced fixation surface, much of the fixation between the bone and the base 500 may result from that bone ingrowth. Further, lateral component 550 provides additional support to the base component 500, as described in greater detail below.

Base 500 includes chisel slots 513 extending through bone-engaging surface 503 to proximal surface 502. Chisel slots 513 are positioned between side wall 504 and anchor 540. Two of the chisel slots have an elongated "U" shape and two of the chisel slots have a substantially trapezoidal shape. Chisel slots 513 are sized and positioned to facilitate a revision procedure after base 500 has been implanted into a patient for an amount of time. Chisel slots 513 allow a surgeon to insert a tool, such as a bone chisel or reamer, into each chisel slot 513 in order to chisel, ream, or otherwise cut away at bone.

Base 500 is adapted to receive an articulating component (not shown) of the stemless implant. In the illustrated example, base 500 may be adapted to couple to a proximal humerus of a patient, with a prosthetic humeral head adapted to couple to the base. In this regard, base 500 includes an opening 525 extending distally into the base from collar 501 for receiving at least a portion of the prosthetic humeral head. The prosthetic humeral head is intended to articulate with a native or prosthetic glenoid of the shoulder joint. The opening may have any shape that suitably mates with the corresponding portion of the prosthetic humeral head.

Base 500 advantageously defines collar 501 having a "shield" shape, as shown in FIG. 8A such that a superior portion is generally rounded and an inferior portion is substantially triangular. The shape of collar 501 may resemble an escutcheon, almond, or tear drop shape. Such shapes are defined by a substantially rounded portion at a first end connected to inwardly tapering sides at an opposite end. Such a shape is in contrast to implants of the prior art which are generally round and substantially circular. Base components with shield shapes, as well as other base components which may be used in the systems described herein, are disclosed in greater detail in U.S. Provisional Application No. 63/021,377, entitled Stemless Metaphyseal Humeral Implant, and filed on May 7, 2020, the disclosure of which is incorporated herein.

Prior bases of stemless shoulder implants have been designed with circular profile. The circular bases of the prior art tend to result in high cortical shell penetration rates because the anatomy of the humerus changes in a distal-inferior direction. In comparison, with the "shield" shape of the base of the present disclosure, the risk of such penetration and thus fracture is reduced because the shield shape mimics the anatomy of the humerus bone.

This shape advantageously allows for penetration of high density zones including the cancellous bone relatively close to the cortical shell without penetrating into the cortical shell.

FIG. 9 shows lateral component 550, which includes head 552 and shaft 554. Head 552 has a wider diameter than shaft 554. Head 552 includes a hex feature which may allow lateral component 550 to thread onto connection member 546 or alternatively provide a counter-torque feature as connection member 546 is threaded into lateral component 550. Shaft 554 is cannulated and includes internal, female threads (not shown) within the cannulation, which are configured to mate with the external, male threads of connection member 546 of base 500.

Figure 10:
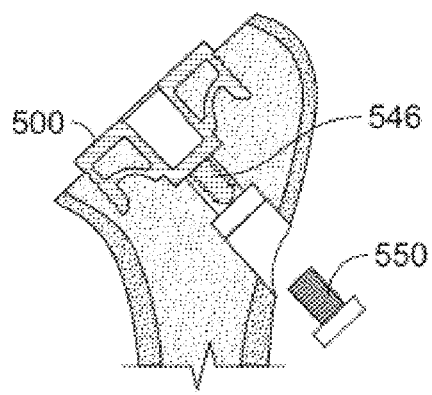
FIG. 10 is a schematic view of the base component and lateral components of FIGS. 8A, 8B, and 9.

In use, as shown in FIG. 10, base component 500 is fixed on the resected plane of the cavity prepared within the proximal humerus. Lateral component 550 is inserted within a prepared passage in the lateral side of the humerus. The passage is created to have a diameter sized to allow shaft 554 of lateral component 550 to pass through but small enough to prevent head 552 from passing through the passage. In one example, lateral component 550 is torqued to engage the internal threads of shaft 554 to the external threads of connection member 546. When in a locked position, the longitudinal axes of the lateral component 550 and the connection member 546 are coaxial. The engagement between the lateral component 550 and base component 500 allows for increased stability of the system. Alternatively, the connection member 546 may be rotated to allow for engagement between the threads.

Figure 11:
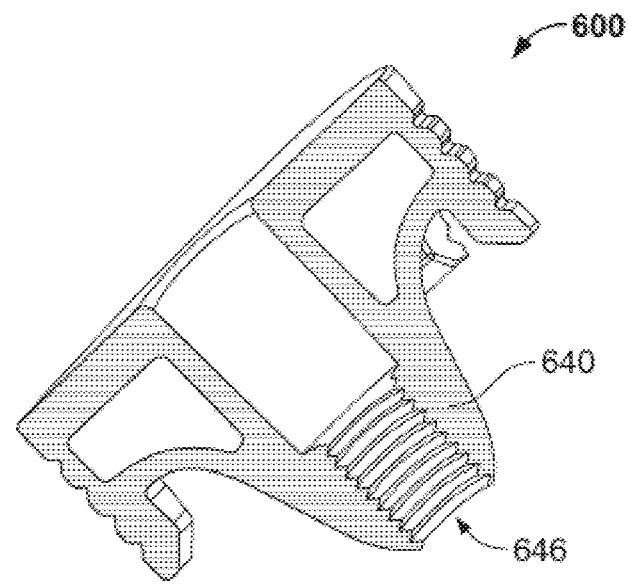
FIG. 11 is a cross-sectional view of a base component in accordance with another embodiment of the present disclosure.
Figure 12:
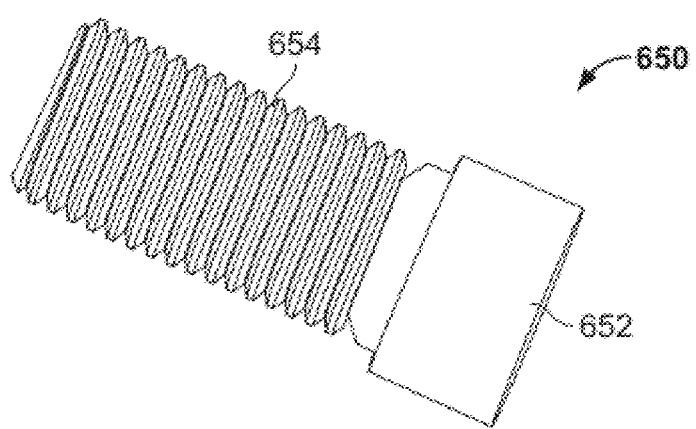
FIG. 12 is a perspective side view of a lateral component for use in conjunction with the base component of FIG. 10.
Figure 13:
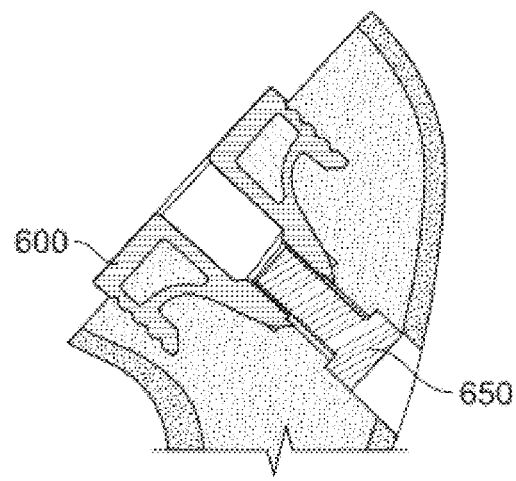
FIG. 13 is a schematic view of the base component and lateral components of FIGS. 11 and 12.
Figure 14:
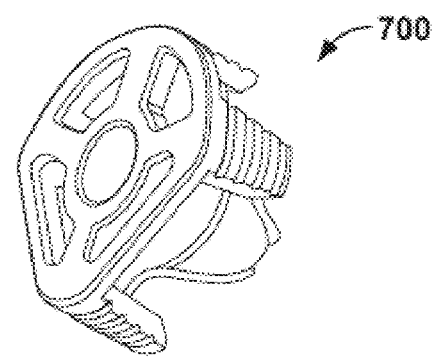
FIG. 14 is a perspective side view of a base component in accordance with another embodiment of the present disclosure.
Figure 15:
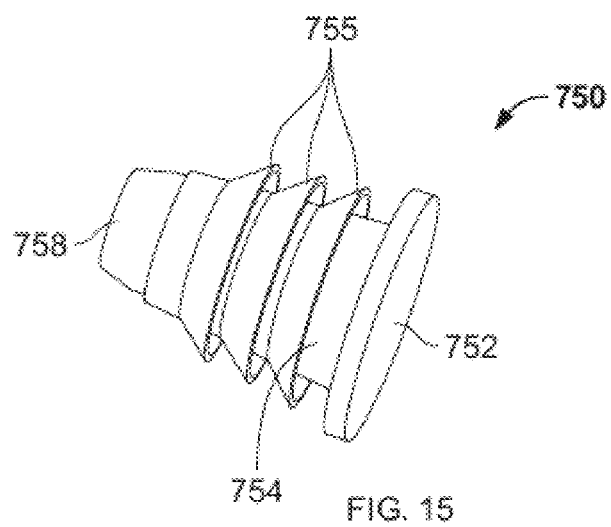
FIG. 15 is a perspective side view of a lateral component for use in conjunction with the base component of FIG. 14.
Figure 16:
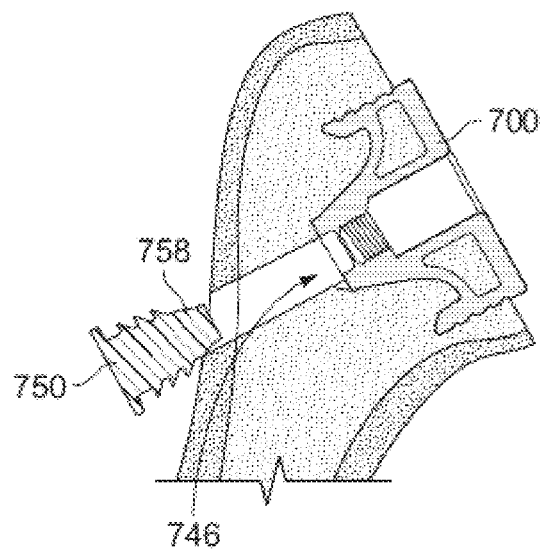
FIGS. 16 and 17 are schematic views of the base component and lateral components of FIGS. 14 and 15.

In an alternative embodiment, shown in FIGS. 11-13, base component 600 includes opening 646 at a distal end of the anchor 640 and extending within at least a portion of the anchor which receives lateral component 650. Opening 646 of the base component 600 includes internal threads, which form the connection member, as the internal threads mate with corresponding outer threads of lateral component 650. As shown in FIG. 12, lateral component 650 includes threaded shaft 654 and head 652. Threaded shaft 654 is externally threaded along at least a portion of the length of the shaft, and advantageously a substantial portion of the entirety of the shaft is threaded to allow for secure engagement to base component 600. In use, as shown in FIG. 13, lateral component 650 is received within base component 600 such that the mating threads engage to lock the two-piece system together.

In the embodiments of FIGS. 8-10 and 11-13, the engagement of the threads locks the two pieces, i.e. base component 500 and lateral component 550, and base component 600 and lateral component 650, together to securely fix the base component within the cavity of the proximal humerus. When attached via the threads, the longitudinal axes of the base component and the lateral component are coaxial. With the application of torque, the base component is further compressed inside the cavity for secure implantation, particularly since the heads 552, 652 of the lateral components are sized larger than the passage within the lateral part of the humerus. These two-piece systems provide for better stability, enhanced initial and long-term fixation, reduced micromotion, and good resistance to torque out and pull out.

Figure 17:
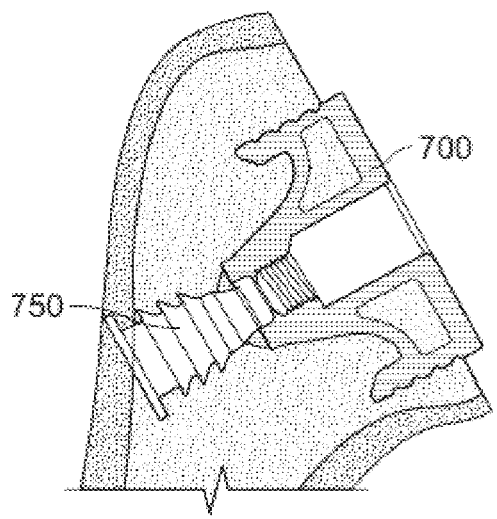

FIGS. 14-17 show another embodiment of a two-piece system including base component 700 and lateral component 750. Base component 700 is substantially similar to base component 600, the similar features of which will not be repeated herein. In this embodiment, lateral component 750 includes head 752 and shaft 754 that tapers inwardly from a first end adjacent head 752 to a second end 758. Shaft 754 attaches to base component 700 at the second end 758 via opening 746 at a distal end of anchor 740 of base component 700, as shown in FIG. 17. Shaft 754 includes a plurality of serrations, ridges, or barbs 755 along its length, each barb extending around the circumference of the shaft. Barbs 755 engage the cortical and/or cancellous bone for additional fixation. Due to the tapered or conical shape of the lateral component, the base component and the lateral component are each pressed into the bone such that the two pieces attach via a taper lock. Further, with barbs 755 and the conical shape of the shaft 755, the lateral component achieves a press-fit with the bone.

Figure 18:
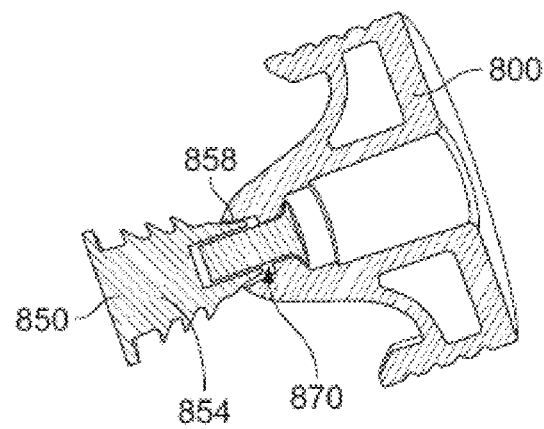
FIG. 18 is a cross-sectional view of a base component and a lateral component of a system in accordance with another embodiment of the present disclosure.
Figure 19:
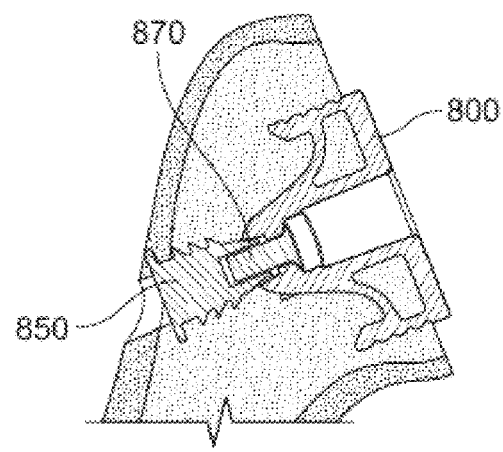
FIG. 19 is a schematic view of the system of FIG. 18.

In another embodiment, shown in FIGS. 18 and 19, the system is of a three-piece construction in which compression screw 870 joins base component 800 and lateral component 850 to one another. In this example, base component 800 is substantially similar to base component 700, and lateral component 850 is substantially similar to lateral component 750, except that second end 858 of shaft 854 of lateral component 800 defines a threaded opening into which compression screw can be received. Compression screw 870 includes outer threads that lock to internal threads of lateral component 850.

In use, as shown implanted in FIG. 19, compression screw 870 is placed within opening 846 of base component 800 and threaded into second end 858 of shaft 854 of lateral component 850. In this manner, compression screw 870 connects base component 800 and lateral component 850 to one another. Lateral component 850 allows for stability of the system while engaging the cortical and/or cancellous bone for additional fixation. Due to the tapered or conical shape of the lateral component, the lateral component achieves a press-fit with the bone.

Although the invention herein has been described with reference to particular embodiments, it is to be understood that these embodiments are merely illustrative of the principles and applications of the present invention. For example, base component 120 of the system may include additional or alternative fixation elements including holes for receiving screws therethrough. Further, it is envisioned that the system not be limited to a stemless shoulder system but can be used in a similar manner with a stemmed shoulder implant as well as other shoulder systems and can also be used in a similar manner with a component of a hip implant or an intramedullary nail to provide immediate fixation while biologic healing and bone ingrowth occurs. It is therefore to be understood that numerous modifications may be made to the illustrative embodiments and that other arrangements may be devised without departing from the spirit and scope of the present invention as defined by the appended claims.

The invention claimed is:

1. A method of fixation for shoulder surgery comprising:
   implanting a base member of a prosthetic stemless shoulder implant into a proximal humerus of a patient;
   passing a drill through a bore of the base member;
   drilling through the humerus to form a passageway from the proximal humerus through a cortical shell of the humerus;
   passing a first fixation device of a fixation construct through the bore of the base member and through the passageway so that the cortical shell is positioned between the base member and the first fixation device;
   placing a second fixation device of the fixation construct in the base member, the first fixation device being coupled to the second fixation device via a flexible member;
   drawing the second fixation device toward the first fixation device;
   tensioning the flexible member to secure the base member to the proximal humerus via the fixation construct; and
   after tensioning the flexible member to secure the base member to the proximal humerus via the fixation construct, attaching a prosthetic humeral head member to the base member by positioning the prosthetic humeral head member within the bore, so that the prosthetic humeral head member overlies the second fixation device to secure the second fixation device within the base member.

2. The method of claim 1, wherein when the first fixation device is passed through the bore of the base member, the first fixation device is in a first orientation.

3. The method of claim 2, further comprising the step of flipping the first fixation device from the first orientation to a second orientation so that a surface of the first fixation device lies flush against the cortical shell of the humerus.

4. The method of claim 3, wherein in the second orientation, the first fixation device is prevented from passing through the passageway.

5. The method of claim 4, wherein in the second orientation the first fixation device extends in a non-parallel direction to the passageway.

6. The method of claim 1, wherein the first fixation device has a minimum dimension less than a first diameter of the bore of the base member such that in the first orientation the first fixation device passes through the bore of the base member.

7. The method of claim 1, wherein during the drawing step, the second fixation device is prevented from passing through the bore of the base member.

8. The method of claim 1, wherein the drawing step decreases a distance between the first fixation device and the second fixation device.

9. The method of claim 1, wherein the flexible member is a suture.

10. The method of claim 9, wherein the suture includes one or more strands that pass through one or more first apertures in the first fixation device and that also pass through one or more second apertures in the second fixation device.

11. The method of claim 10, wherein the one or more strands form loops at the first fixation device and free ends of the one or more strands extend out of the second fixation device.

12. The method of claim 10, wherein the one or more strands form loops at the second fixation device and free ends of the one or more strands extend out of the first fixation device.

13. The method of claim 1, wherein passing the first fixation device of the fixation construct through the bore of the base member and through the passageway includes passing a lead suture through the bore of the base member and through the passageway, the lead suture having a first end coupled to the first fixation device.

14. The method of claim 13, wherein passing the lead suture through the bore of the base member and through the passageway includes passing a needle through the bore of the base member and through the passageway, the needle being coupled to a second end of the lead suture.

15. The method of claim 1, further comprising locking the fixation construct after tensioning the flexible member.

16. The method of claim 15, wherein locking the fixation construct comprises tying at least one locking knot with the flexible member extending proximally to the second fixation device.

17. The method of claim 15 wherein locking the fixation construct comprises tying at least one locking knot with the flexible member extending distally to the first fixation device.

18. The method of claim 17, wherein the tying step includes tying three locking knots.

\* \* \* \* \*